US005514873A

United States Patent [19]
Schulze-Ganzlin et al.

[11] Patent Number: 5,514,873
[45] Date of Patent: May 7, 1996

[54] X-RAY APPARATUS HAVING A CABLE-FREE PORTABLE RADIATION DETECTOR WITH A HOUSING FOR THE ACCEPTANCE OF A RADIATION TRANSDUCER

[75] Inventors: Ulrich Schulze-Ganzlin, Lorsch; Josef Ploetz, Bensheim, both of Germany

[73] Assignee: Siemens Aktiengesellschaft, Munich, Germany

[21] Appl. No.: 374,025

[22] Filed: Jan. 18, 1995

[30] Foreign Application Priority Data

Jan. 25, 1994 [DE] Germany .................... 44 02 114.3

[51] Int. Cl.⁶ ................. G01T 1/00; H05E 1/30
[52] U.S. Cl. ............. 250/394; 250/370.09; 250/370.11; 378/102; 378/116
[58] Field of Search ............ 250/370.11, 370.09; 378/102, 116

[56] References Cited

U.S. PATENT DOCUMENTS

| | | |
|---|---|---|
| 4,082,953 | 4/1978 | Krause et al. . |
| 4,856,036 | 8/1989 | Malcolm et al. ............... 378/166 |
| 4,912,735 | 3/1990 | Beer . |
| 4,979,198 | 12/1990 | Malcolm et al. ............... 378/102 |
| 5,134,639 | 7/1992 | Vekstein et al. . |
| 5,140,696 | 8/1992 | Fox . |
| 5,187,380 | 2/1993 | Michon et al. ............... 250/370.09 |
| 5,235,191 | 8/1993 | Miller ............... 250/370.09 |
| 5,331,166 | 7/1994 | Yamamoto et al. . |

FOREIGN PATENT DOCUMENTS

| | | |
|---|---|---|
| 0544974 | 6/1993 | European Pat. Off. . |
| 4225220 | 2/1994 | Germany ............... 250/370.11 |
| 2093352 | 4/1990 | Japan ............... 250/370.11 |

*Primary Examiner*—Constantine Hannaher
*Assistant Examiner*—Virgil O. Tyler
*Attorney, Agent, or Firm*—Hill, Steadman & Simpson

[57] ABSTRACT

An x-ray apparatus has a portable radiation detector having a housing containing a radiation transducer formed of individual detector cells that convert incident radiation, particularly x-radiation, into electrical signals. The radiation detector is implemented cable-free. A wireless transceiver for the infeed of operating energy and for the outfeed of the signals is provided. An advantage of this radiation detector is the cable-free construction, and the simple manipulation and reusability resulting therefrom. Moreover, the radiation detector is better suited to hygienic demands.

18 Claims, 1 Drawing Sheet

X-RAY APPARATUS HAVING A CABLE-FREE PORTABLE RADIATION DETECTOR WITH A HOUSING FOR THE ACCEPTANCE OF A RADIATION TRANSDUCER

BACKGROUND OF THE INVENTION

1. Field of the Invention

The present invention relates to high-energy radiation detectors and in particular to a portable radiation detector of the type having a housing containing a radiation transducer.

2. Description Of the Prior Art

German OS 25 19 640 discloses a dental x-ray diagnostics installation that has an automatic exposure unit for controlling the radiation generator in order to obtain an optimum exposure of an x-ray film. For producing an x-ray exposure, a film holder is arranged in the mouth of a patient, this film holder carrying a dental x-ray film in a pocket. A detector/transmitter circuit that wirelessly emits an electrical signal corresponding to the film blackening is adjacent to the pocket. This signal is received by an antenna and is supplied to the automatic exposure unit which controls the radiation source. The automatic exposure unit effects a turn-off of the radiation when the dose corresponding to the desired film blackening has been reached.

The detector/transmitter circuit is fashioned as an integrated component and includes a phosphor layer behind which a light-sensitive detector is arranged. The phosphor layer is excited to luminesce dependent on the incident radiation dose. The light emitted by the phosphor layer is converted into an electrical output signal by the detector, this electrical output signal thus being a measure for the radiation intensity. The output signal is amplified in an amplifier and integrated in an integrator. The integrator is followed by a trigger circuit whose threshold can be set with a reference value generator to correspond to the sensitivity of the x-ray film. The trigger circuit controls the activation and deactivation of the transmitter. A voltage supply is provided in the detector/transmitter circuit that contains a switch with which the operating voltage can be connected to the components. It is known that a detector that is directly sensitive for x-rays can also be employed.

European Application 0 544 974 discloses a radiation detector constructed with a CCD converter whose individual detector cells generate output signals dependent on incident radiation. These output signals can be supplied to a computational unit that, for example, produces a fluoroscopic image of a subject on a monitor. The CCD converter is connected via an electrical line and/or via fiber optics to an isolating unit in which the signals are electrically decoupled and are supplied via a cable to a computer serving as computational unit. The employment of electrical lines and/or fiber optics is simple and is thus less cost-intensive; moreover, external disturbances are effectively shielded or are least reduced to a minimum. The infeed and outfeed of the signals as well as the voltage supply of the CCD converter ensues via the isolating unit and via the cable or the fiber optics.

German OS 42 35 527 discloses a signal acquisition device containing a CCD which is connected to a control unit arranged outside the acquisition device. The signals of the CCD are transmitted via a cable to detector circuitry arranged outside the control unit.

Computed tomography systems are disclosed in U.S. Pat. No. 4,912,735, U.S. Pat. No. 5,140,696 and U.S. Pat. No. 5,134,639. Such computed tomography systems have a radiation detector with individual detector cells connected to one another that convert incident radiation into signals. The signals are inductively transmitted according to U.S. Pat. No. 4,912,735, capacitively transmitted according to U.S. Pat. No. 5,140,696 and electro-optically transmitted according to U.S. Pat. No. 5,134,639.

SUMMARY OF THE INVENTION

An object of the invention is to implement a radiation detector for use in an x-ray installation, the radiation detector being economically manufacturable, having a compact structure and being reusable.

The above object is inventively achieved in an x-ray installation having a portable radiation detector with a housing for the acceptance of a radiation transducer that has individual detector cells that convert incident radiation, particularly x-radiation, into electrical output signals and which consumes operating energy in doing so, the radiation detector having cable-free means for the infeed of operating energy and for the outfeed of the output signals.

An advantage of the x-ray installation of the invention is the cable-free execution of the radiation detector, this being possible because wireless means for the infeed of energy and for the outfeed of signals are provided. This radiation detector thus has a compact structure, is reusable and is therefore economic in terms of manufacture and maintenance. Due to the cable-free execution, the radiation detector can be manipulated in a simple way; moreover, it is more suited to hygienic demands than a radiation detector implemented with a cable.

DESCRIPTION OF THE PREFERRED EMBODIMENTS

Figure 1:
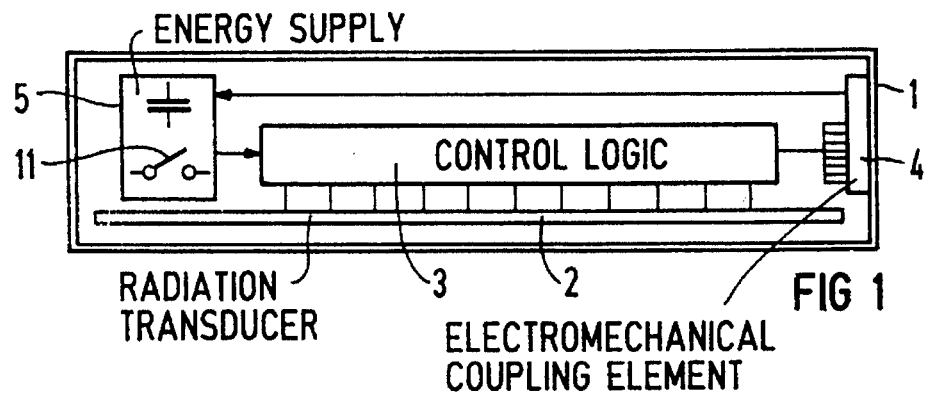
FIG. 1 is a schematic illustration of a first exemplary embodiment of a radiation detector of an x-ray diagnostics apparatus of the invention.
Figure 3:
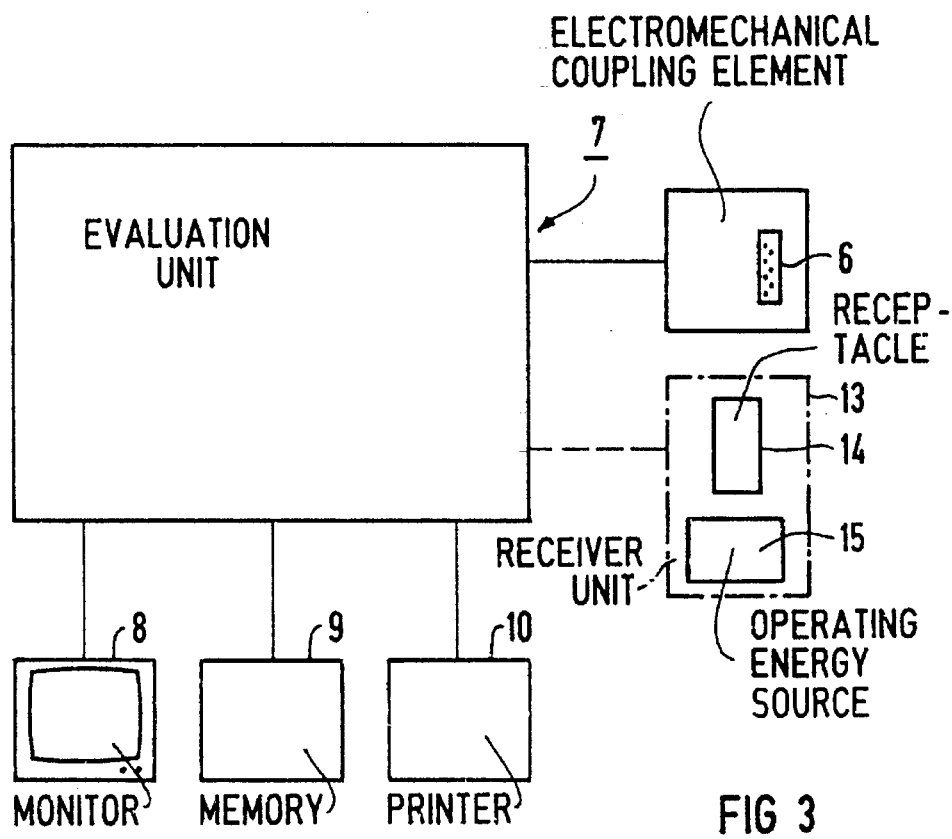
FIG. 3 is a block diagram of an evaluation unit of an x-ray diagnostics apparatus for evaluating the signals of the radiation detectors of FIGS. 1 and 2.

A radiation detector is shown in FIG. 1 is preferably portable and has an essentially rectangular housing 1 in which a radiation transducer 2 as well as wireless means for receiving operating energy, preferably the supply voltage, and for the outfeed of the signals are arranged. The radiation detector is part of a radiation detector system, the peripheral components of the system being shown in FIG. 3.

The radiation transducer 2 has individual detector cells that convert incident radiation, particularly x-radiation, into electrical signals either directly or in combination with a phosphor layer. The signals of the radiation transducer 2 are conducted via a control logic 3 to an electro-mechanical coupling element 4. Insofar as the radiation transducer 2 as well as the control logic 3 require an energy supply 5, this can likewise be arranged in the housing 1. This energy supply 5 can be implemented as a conventional battery, however, it is also possible to provide a re-chargeable battery that is connected to the electro-mechanical coupling element 4. The housing 1 can be implemented as a single-part or multi-part injection molded plastic part.

For producing an x-ray exposure, the radiation detector–if it is being used, for example, in a matter of a radiation detector system for diagnostics in dental medicine–is arranged in the mouth of a patient. After having penetrated, for example, a tooth, the ray beam emanating from a radiation transmitter is incident on the radiation transducer 2 in the form of radiation shadow of the tooth, and the individual detector cells of the radiation transducer 2 generate signals dependent upon the incident ray shadow. After the radiation detector has been removed from the mouth, it is coupled via the electro-mechanical coupling element 4 to a further electro-mechanical coupling element 6 of an evaluation unit 7 shown in FIG. 3, and the signals are read out from the radiation detector. For example, a plug/socket means is suitable as the electro-mechanical coupling elements 6 and 8. On the basis of these signals, the evaluation unit 7 calculates image signals of a fluoroscopic image of the tooth, these signals being capable of display on a monitor 8, or storage in a memory 9 or conversion to a hard copy in a printer 10. After the read-out of the signals, the information in the individual detector cells is quenched. This can ensue by the infeed of energy, for example, via the evaluation unit 7, or by actuating a switch 11 provided in the energy supply 5. After being uncoupled from the evaluation unit 7, the radiation detector is again available for producing a new x-ray exposure.

Figure 2:
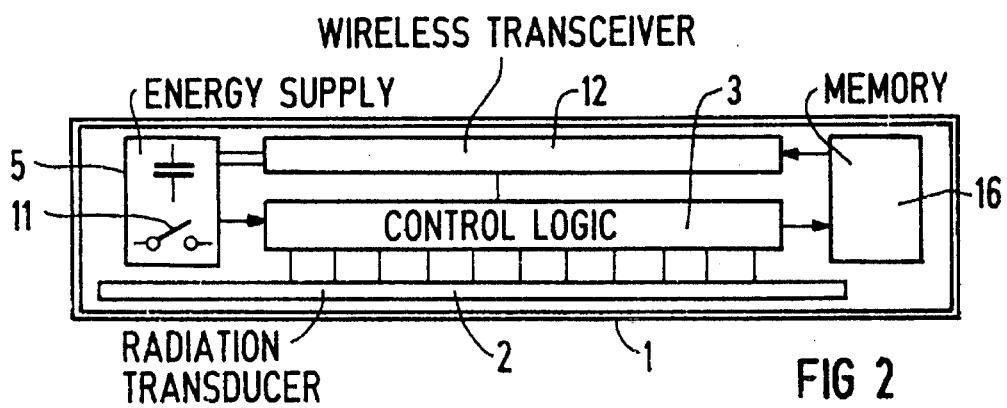
FIG. 2 is a schematic illustration of a second exemplary embodiment of a radiation detector of an x-ray diagnostics apparatus of the invention.

In the radiation detector shown in FIG. 2, elements that already have a reference character in FIG. 1 are identified with the same reference character. Instead of an electromechanical coupling element 4, the detector of FIG. 2 has wireless means for the infeed of energy, preferably the supply voltage, and for the outfeed of the signals. The wireless means are formed by a wireless signal transceiver 12. The transceiver 12 may include signal converters, modulators and demodulators, and interfaces, as may be needed. The transceiver is supplied with the signal of the control logic 3. The signals of the control logic 3 are communicated via the transceiver 12, for example inductively, capacitively or electro-optically, to a reception unit 13 shown with dashed lines in FIG. 3. An energy store of the energy supply 5 can also be charged by infeeding energy via the transceiver 12. In order to enable the infeed of the supply voltage and the outfeed of the signals with the lowest loss as possible and without a high energy consumption, it is provided that the reception unit 13 has a receptacle 14 for the housing 1 into which the latter can be introduced, the reception unit 13 containing (or being connected or connectable to) a source 15 for the operating energy.

The housing 1 in the embodiment of FIG. 2 can be completely closed, i.e., having no terminals or connectors thereon. A memory 16 can be provided in the housing 1 within the scope of the invention, the signals of the radiation transducer 2 being supplied to this memory 16. This embodiment is advantageous when the signals of the radiation transducer 2 are not temporally stable. Radiation transducers that modify their chemical or physical properties as a consequence of incident radiation can also be employed as the radiation transducer 2 for generating electrical signals instead of CCD converters. After the physical or chemical modification has been detected and read out, the original condition of these radiation transducers is thereby restored by infeeding energy. When a memory 16 is provided, it is advantageous for the memory 16 not only to store signals corresponding to one x-ray exposure but also to store signals corresponding to a plurality of x-ray exposures. After a first x-ray exposure, thus, the signals of, for example, the CCD converter can thus be read into the memory 16. After the original physical condition of the CCD converter has been restored, a new x-ray exposure can ensue. The signals of the CCD converter corresponding to the new x-ray exposure can then likewise be stored in the memory 16. After the conclusion of the x-ray exposures, the signals of the memory 16 are then read out via the evaluation unit 7 and processed.

The advantages of this radiation detector are the cable-free infeed and outfeed of signals and the cable-free infeed of the supply voltage as well as, additionally, the complete encapsulation that is significant from a hygienic point of view as well as the abandonment of an exposed electro-mechanical coupling means. The radiation detector of the invention, of course, can be employed not only in a dental x-ray diagnostics installation but also can be employed in a general purpose x-ray diagnostics installation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A radiation detector system for use in an x-ray apparatus having a source of operating energy, said radiation detector system comprising:

a housing;

a radiation transducer disposed in said housing composed of a plurality of detector cells which convert a shadow image formed by incident x-rays into electrical signals from which said shadow image is recreatable and which consumes operating energy; and cable-free means in said housing connected to said radiation transducer for infeeding operating energy to said radiation transducer from said operating energy source and for outfeeding said electrical signals.

2. A radiation detector system as claimed in claim 1 wherein said housing is closed, and wherein said cable-free means comprises means for inductively infeeding said operating energy and for inductively outfeeding said electrical signals.

3. A radiation detector system as claimed in claim 1 wherein said housing is closed, and wherein said cable-free means comprises means for capacitively infeeding said operating energy and for capacitively outfeeding said electrical signals.

4. A radiation detector system as claimed in claim 1 wherein said housing is closed, and wherein said cable-free means comprises means for electro-optically infeeding said operating energy and for electro-optically outfeeding said electrical signals.

5. A radiation detector system as claimed in claim 1 wherein said cable-free means comprises an electro-mechanical connector disposed on said housing.

6. A radiation detector system as claimed in claim 1 wherein said radiation transducer comprises a CCD converter.

7. A radiation detector system as claimed in claim 1 further comprising means in said housing, connected to said cable-free means and to said radiation transducer, for storing said operating energy after infeed of said operating energy from said operating energy source.

8. A radiation detector system as claimed in claim 1 further comprising memory means in said housing connected to said radiation transducer and to said cable-free means for storing said electrical signals.

9. A radiation detector system as claimed in claim 8 wherein said memory means comprises means for storing respective electrical signals from a succession of different x-ray exposures.

10. A radiation detector system as claimed in claim 1 further comprising control means in said housing connected to said cable-free means and to said radiation transducer for controlling infeed of said operating energy and outfeed of said electrical signals.

11. A radiation detector system as claimed in claim 1 wherein said housing comprises a housing adapted for arrangement in a human mouth for obtaining a dental x-ray image as said shadow image.

12. A radiation detector system as claimed in claim 1 further comprising evaluation means for evaluating said electrical signals, and means for coupling said evaluation means to said radiation detector via said cable-free means.

13. A radiation detector system as claimed in claim 12 wherein said means for coupling comprises means for wirelessly coupling said evaluation means to said radiation detector.

14. A radiation detector system as claimed in claim 12 wherein said evaluation means comprises a display unit and means for producing a fluoroscopic image on said display unit from said electrical signals.

15. A radiation detector system as claimed in claim 12 wherein said evaluation means includes means for quenching said radiation transducer when said evaluation means and said radiation detector are coupled.

16. A radiation detector system as claimed in claim 12 wherein said means for coupling comprises electro-mechanical means for coupling said evaluation means to said radiation detector.

17. A radiation detector system as claimed in claim 12 wherein said evaluation means includes reception means containing said coupling means.

18. A radiation detector system as claimed in claim 17 wherein said reception means has a housing with a receptacle therein for receiving said housing of said radiation detector to effect coupling of said radiation detector and said evaluation means via said coupling means.

* * * * *